United States Patent [19]

Hata et al.

[11] Patent Number: 4,609,492

[45] Date of Patent: Sep. 2, 1986

[54] PERFUME COMPOSITION CONTAINING AN UNSATURATED ALIPHATIC CARBOXYLIC ACID

[75] Inventors: Go Hata, Fujisawa; Takeaki Etoh, Noda; Toshifumi Shirakawa, Noda; Yuji Matsuura, Noda; Takashi Uchiyama, Koshigaya, all of Japan

[73] Assignee: Soda Aromatic Company, Limited, Tokyo, Japan

[21] Appl. No.: 751,626

[22] Filed: Jul. 2, 1985

Related U.S. Application Data

[63] Continuation of Ser. No. 432,870, Oct. 5, 1982, abandoned.

[30] Foreign Application Priority Data

Oct. 6, 1981 [JP] Japan .................. 56-158134

[51] Int. Cl.$^4$ .................................. A61K 7/46
[52] U.S. Cl. ........................... 252/522 R; 260/405.5; 260/413; 562/545; 426/534
[58] Field of Search ............... 252/522 R; 260/544, 260/405.5, 413 R; 562/545; 426/534

[56] References Cited

PUBLICATIONS

Martinez et al., CA 97:38703x (1982).
Kita, J. Org. Chem. 22, 436–8 (1957).
Arctander, *Perfume and Flavor Chemicals*, Monographs 843 and 3049 (1967).

*Primary Examiner*—Anton H. Sutto
*Attorney, Agent, or Firm*—Scully, Scott, Murphy & Presser

[57] ABSTRACT

Provided is a perfume composition containing a straight-chain trans-6-alkenoic acid represented by the general formula

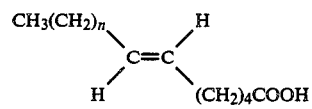

wherein n is an integer of 1 to 4.

2 Claims, No Drawings

PERFUME COMPOSITION CONTAINING AN UNSATURATED ALIPHATIC CARBOXYLIC ACID

CROSS REFERENCE TO RELATED APPLICATION

This appliction is a continuation of our copending application Ser. No. 432,870, filed Oct. 5, 1982, now abandoned.

BACKGROUND OF THE INVENTION

The present invention relates to a perfume composition and more particularly to a perfume composition containing a odorous component which has a milky odor.

A few compounds such as acyllactic acid thioesters have heretofore been known to have an odor similar to that of natural milk. These compounds having a milky odor have been added, as a component of mixed perfumes, to dairy products such as butter and milk, and are now in increasing demand.

Under the circumstances, development of an odorous component which has a superior milky odor characteristics and which is inexpensive, is desired.

SUMMARY OF THE INVENTION

It is an object of the present invention to provide a novel perfume composition containing a odorous component which has a superior milky odor characteristics and which is easy to manufacture.

More precise objects and advantages of the present invention will become apparent from the following description.

We have searched for such a milky aroma component and found that an unsaturated carboxylic acid with a specific structure, i.e., a straight-chain trans-6-alkenoic acid represented by the following general formula (I):

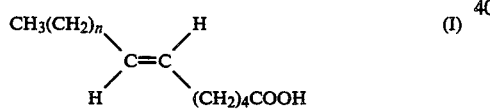

wherein n is an integer of 1 or 4, has a superior milky odor.

The straight-chain trans-6-alkenoic acid represented by the above general formula (I), which is an odorous component used in the present invention, has a characteristic odor not found in compounds having chemical structures similar thereto. For example, a straight-chain alkenoic acid which has a double bond in any other position than the 6-position does not have milky odor. Even in the case of a straight-chain 6-alkenoic acid, the cis isomer does not have milky odor. Only the cis isomer, straight-chain alkenoic acid which has a trans double bond on the 6-position has such a milky odor characteristics.

Thus, the characteristics of the straight-chain trans-6-alkenoic acid of the present invention is quite selective. The use of the compound as one component or an odorous component of a perfume composition gives the resultant perfume composition a remarkably milky odor, an enhanced milky odor, or a mild impression derived from a milky odor.

As other components of the perfume composition, there may be used conventional perfume components such as other kinds of perfumes and diluents according to purposes of use.

The straight-chain trans-6-alkenoic acid of the present invention is preferably used as one odor component of, for example, fragrances, food flavors, feed flavors and tobacco flavors. As it has a superior milky odor, it is more effectively used as an odor component of flavors for dairy products.

The amount of the straight-chain 6-alkenoic acid in the perfume composition of the present invention is usually in the range of 0.01 to 10 wt.% although it somewhat differs according to purposes of use, etc.

The straight-chain trans-6-alkenoic acid used in the present invention can be easily prepared by known methods, for example, by the method described in J. Med. Chem., 1967, 10, 533, and J. Med. Chem., 1971, 14(3), 236, or by the following method:

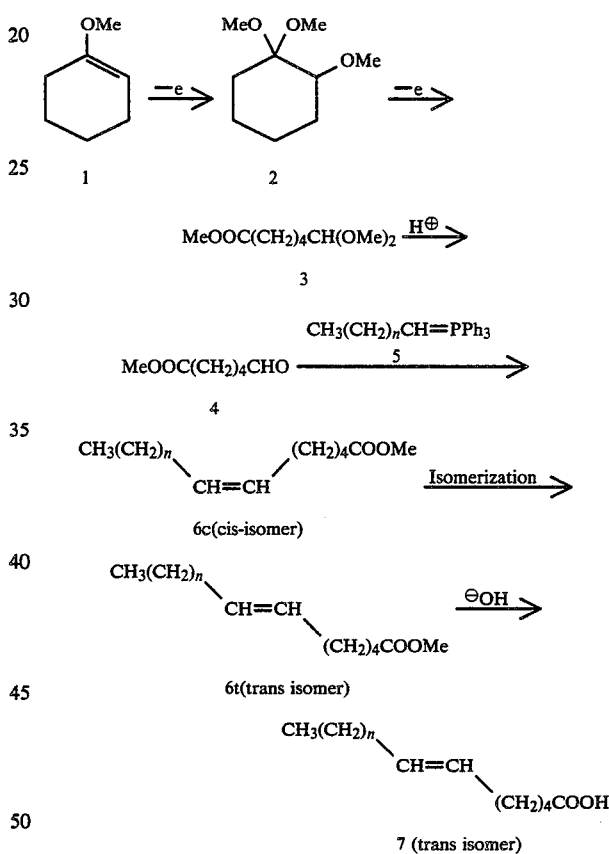

wherein n is an integer of 1 to 4 and Me is methyl group. As shown above, methyl ether of cyclohexene 1 is converted to trimethoxy compound 2 by electrolytic oxidation, to acetal ester 3 by further electrolytic oxidation and then to aldehyde ester 4 by acidic hydrolysis, which is subjected to Wittig reaction with ylide 5 derived from phosphonium salt to give cis-6-alkenoic acid methyl ester 6c, which is then isomerized by using a catalytic amount of para-toluenesulfinic acid into trans-6-alkenoic acid methyl ester 6t, followed by alkaline hydrolysis to give trans-6-alkenoic acid 7.

In some particular manufacturing method, in addition to trans isomer of the straight-chain 6-alkenoic acid, there may be incorporated its cis isomer. Although the cis isomer does not have a milky odor, the incorporation of the cis isomer in the perfume composition, it does not give the odor of the composition any bad effect. Therefore, even in an incorporated state of the cis isomer, the straight-chain trans-6-alkenoic acid may be used as an odorous component. In this case, it is desirable that the content of the cis isomer be not more than half of the entire straight-chain 6-alkenoic acid.

Working examples of the present invention are given below to further illustrate the invention, but it is to be understood that the invention is not limited thereto.

EXAMPLE 1

Preparation of trans-6-decenoic acid 1.07 g. of a commercially available 50% sodium hydride was placed in a flask. After washing it several times with n-pentane, 20 ml. of dry dimethyl sulfoxide (DMSO) was dropped, then heated at 75°–80° C. with stirring until evolving of hydrogen ceased. After cooling, a solution of 9.25 g. n-butyltriphenylphosphonium bromide in 10 ml. DMSO was added, and followed to drop 3.20 g. of 5-carbomethoxy-1-pentanal during 10 minutes, then stirred for 30 minutes. After reaction, water was added and the reaction mixture was extracted with ether, followed by washing twice with brine. After drying, the solvent was recovered to give crude products. By the purification with column chromatography 1.43 g. of methyl cis-6-dodecenoate was obtained. The solution of it in 50 ml. of anhydrous dioxane was refluxed together with 0.96 g. of p-toluenesulfinic acid anhydride for 1 hour. Then, the solvent was recovered under reduced pressure and the reaction product was treated by usual method. By column chromatography 0.86 g. of methyl trans 6-decenoate was obtained, subsequently submitted to hydrolysis using alkali to afford 0.75 g. of trans 6-decenoic acid.

Trans 6-nonenoic acid, trans 6-undecenoic acid and trans-6-dodecenoic acid can also be prepared in the same method.

The 5-carbomethoxy-1-heptanal used herein was prepared in the following manner.

Preparation of 5-carboxymethoxy-1-heptanal 10.00. g. of 1-methoxy-1-cyclohexene was dissolved in 80 ml. MeOH containing 4.82 g. of sodium methoxide as a supporting electrolyte.

The solution were electrolyzed under a constant current (3A, 3.5 F/mol) in an undevided cell equipped with two carbon electrodes (50 cm$^2$). The solution was condensed under reduced pressure, taken up in ether, washed with water and dried. After evaporation of the solvent crude 1,1,2-trimethylcyclohexane, 8.83 g. was obtained. This crude products was electrolyzed again with same cell and electrodes under the following condition; supporting electrolyte; tetramethyl ammonium p-toluenesulfonate, 2.69 g., solvent; MeOH 80 ml., constant current; 3A 6 F/mol., temperature; room temperature.

After the reaction, MeOH was recovered, following by the same treatment as above to give 9.47 g. of crude 6,6-dimethoxycaproic acid methyl ester. Then, a 10 wt.% aqueous hydrochloric acid solution was added to this crude product, followed by stirring for 6 hours at room temperature. The reaction mixture was treated by usual method to give crude products. Pure 3.20 g. of 5-carbomethoxy-1-pentanal was obtained by column chromatography.

EXAMPLE 2

10 parts of trans-6-decenoic acid was added to a regular milk flavor base of the following formulation:

|  | (parts by weight) |
| --- | --- |
| Dimethyl sulfide | 0.1 |
| Diacetyl | 2 |
| Butyl butyrate | 2.5 |
| Acetoin | 15 |
| Butyric acid | 0.4 |
| Caprylic acid | 20 |
| Maltol | 5 |
| γ-Octalactone | 10 |
| δ-Decalactone | 15 |
| δ-Dodecalactone | 20 |
| Glycerin | 200 |
| Ethyl alcohol | 700 |
| Total: | 990 |

The resulting milk flavor base were submitted to an organoleptic evaluation. All of ten experienced panel members evaluated that the added product was better on the point that a mild sweetness resembling natural milk was emphasized.

EXAMPLE 3

10 parts of trans-6-dodecenoic acid was added to 990 parts of the regular milk flavor base described in Example 2.

All of the panel members evaluated that the composition obtained by the addition showed green odor resembling natural milk.

EXAMPLE 4

10 parts of trans-6-undecenoic acid was added to 990 parts of the regular milk flavor base described in Example 2. All of the panel members evaluated that rich milky odor found in natural milk was enhanced in the resulting flavor as compared to the non-added one.

EXAMPLE 5

10 parts of trans-6-nonenoic acid was added to 990 parts of the regular milk flavor base described in Example 2. The resulting milk flavor was evaluated by the panel member that milky odor with sweetness was enhanced.

EXAMPLE 6

| A tobacco flavor of the following composition was prepared: | |
| --- | --- |
|  | (part by weight) |
| Black tea extract | 20.0 |
| Coffee extract | 30.0 |
| Rum (50°) | 450.0 |
| Ethyl stearate | 10.0 |
| Ethyl oleate | 10.0 |
| Anisole | 3.0 |
| δ-Decalactone | 0.1 |
| Maltol | 5.0 |
| Veratraldehyde | 10.0 |
| St. Johns bread alcohol extract | 210.0 |
| Fennel oil | 1.0 |
| 95% Ethyl alcohol | 100.0 |
| Water | 140.9 |
| Total: | 999.0 |

The prepared flavor of the above composition and the flavor obtained by adding thereto 1.0 part of the trans-6-decenoic acid of the present invention were incorporated respectively with a micro syringe in amounts of 0.01 to 1.0 wt.% into shredded leaves or filter of a commercially available cigarette for the evaluation of the smoking taste. As a result of comparison by ten experienced panel members, all of them evaluated that in the case of the tobacco to which had been added the compound of the present invention, the tobacco-like smoking aroma was enhanced, particularly the smoke from the tobacco became smooth, the stimulation and other undesirable tastes, including bad smell, bitterness, astringency and pungency, were decreased, and a mild and light smoking taste was obtained.

EXAMPLE 7

A floral type composition was prepared according to the following formulation:

|  | (part by weight) |
| --- | --- |
| Linalool | 50 |
| Linalyl acetate | 20 |
| Benzyl acetate | 90 |
| Terpineol | 30 |
| Geraniol | 70 |
| Citronellol | 70 |
| Phenylethyl alcohol | 80 |
| Geranium Bourbon | 10 |
| Lyral (IFF) | 30 |

-continued

|  | (part by weight) |
| --- | --- |
| Eugenol | 70 |
| Jasmine compound | 50 |
| Methyl ionone | 100 |
| p-Tertiary butyl cyclohexylacetate | 30 |
| α-Amylcinnamic aldehyde | 150 |
| Vertfix (IFF) | 50 |
| Musk ketone | 50 |
| Total; | 950 |

The above composition and a composition obtained by adding thereto 50 parts of trans-6-decenoic acid were submitted to an organoleptic evaluation.

All of the ten experienced panel members evaluated that the addition of trans 6-decenoic acid developed sweetness and mildness in the fragrance of the composition.

What is claimed is:

1. A perfume composition which comprises as an essential active ingredient an effective fragrance- and-/or flavor-modifying amount of trans-6-decenoic acid in association with conventional perfume or flavor components.

2. A process for enhancing, improving or modifying the fragrance or flavor properties of perfumes or flavors which comprises the step of admixing in said perfumes or flavors an effective fragrance- and/or flavor-modifying amount of trans-6-decenoic acid.

* * * * *